United States Patent
Kuma et al.

(10) Patent No.: US 7,439,404 B2
(45) Date of Patent: Oct. 21, 2008

(54) PROCESS FOR PRODUCTION OF CUMENE HYDROPEROXIDE

(75) Inventors: Keiji Kuma, Kamisu (JP); Takanori Suzuki, Kurashiki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/591,439

(22) PCT Filed: Mar. 3, 2005

(86) PCT No.: PCT/JP2005/003599

§ 371 (c)(1),
(2), (4) Date: Jun. 6, 2007

(87) PCT Pub. No.: WO2005/085191

PCT Pub. Date: Sep. 15, 2005

(65) Prior Publication Data

US 2007/0260093 A1    Nov. 8, 2007

(30) Foreign Application Priority Data

Mar. 4, 2004 (JP) .............................. 2004-060904

(51) Int. Cl.
*C07C 409/00* (2006.01)
*C07C 407/00* (2006.01)
(52) U.S. Cl. ...................................... 568/568; 568/569
(58) Field of Classification Search ................. 568/568, 568/569
See application file for complete search history.

(56) References Cited

U.S. PATENT DOCUMENTS

| 5,767,322 A | 6/1998 | Zakoshansky et al. | ...... 568/571 |
| 6,043,399 A | 3/2000 | Amadio et al. | ............. 568/574 |

FOREIGN PATENT DOCUMENTS

| EP | 816335 A1 | 7/1959 |
| EP | 712392 A1 | 6/1998 |
| JP | 8-511030 | 11/1996 |
| JP | 10-87609 A | 4/1998 |
| JP | 2000-63352 A | 2/2000 |
| JP | 2003-231674 A | 8/2003 |
| JP | 2003-327576 A | 11/2003 |
| WO | 95/4717 A1 | 2/1995 |

OTHER PUBLICATIONS

International Search Report of PCT/JP2005/003599, mailed May 31, 2005.

*Primary Examiner*—Sikarl A Witherspoon
(74) *Attorney, Agent, or Firm*—Nixon & Vanderhye P.C.

(57) ABSTRACT

A process for the continuous production of cumene hydroperoxide (CHP) by oxidizing cumene in a liquid phase in a reactor in the presence of an oxygen-containing gas, wherein the oxygen content of the whole gas fed into the liquid phase in the reactor is adjusted to 22 to 50 mol % and the oxidation is carried out under the condition that: (1) the CHP production per unit volume of the reaction fluid in the reactor is at least 22 kg/m$^3$/hr, (2) the oxygen content of the exhaust gas from the reactor is 2 to 10 mol %, or (3) the oxygen-containing gas is fed into the reactor by the use of a sparger whose aperture pitch is at least twice the aperture diameter. The process enhances CHP production per unit volume of the reaction fluid in the reactor, thus downsizing the reactor permitting required CHP production or enabling increased CHP production in an existing reactor.

13 Claims, No Drawings

PROCESS FOR PRODUCTION OF CUMENE HYDROPEROXIDE

This application is the U.S. national phase of international application PCT/JP2005/003599, filed 3 Mar. 2005, which designated the U.S. and claims priority of JP 2004-060904, filed 4 Mar. 2004, the entire contents of each of which are hereby incorporated by reference.

TECHNICAL FIELD

The present invention relates to a process for production of cumene hydroperoxide. More particular, it relates to a process for production of cumene hydroperoxide by liquid phase oxidation of cumene which process is capable of significantly enhancing the cumene hydroperoxide production per unit volume of reaction fluid into a reactor by feeding of an oxygen-containing gas having higher oxygen content.

BACKGROUND ART

Cumene hydroperoxide (hereinafter may abbreviate "CHP") is a precursor of phenol production process using cumene process and is produced by liquid phase oxidation of cumene.

Two CHP production processes by liquid phase oxidation of cumene have been known. One is carried out without catalyst (refer to patent document 1), the other is carried out with catalyst (refer to patent document 2). Both processes use an oxygen-containing gas as oxidizing agent fed into a reactor. Usually, air (oxygen content is around 21%) is used as the oxygen-containing gas from the industrial standpoint of safety because high oxygen content of oxygen-containing gas leads to the possibility of explosion and standpoint of cost performance. Under the present situation, even though pure oxygen is used, oxygen is diluted to an oxygen-containing gas having low oxygen content (equal to or lower than the oxygen content of air) and fed into the reactor.

Patent document 1: Japanese Patent No. 3107409
Patent document 2: Japanese Patent No. 3061394

DISCLOSURE OF THE INVENTION

In order to improve the yield of CHP, some technical studies on setting of reaction conditions such as temperature, residence time, pressure (refer to patent document 1) and pH (refer to patent document 2) have been investigated. However still further improvement is required. Especially, from the industrial point of view, miniaturizing of the reactor is highly expected by increasing CHP production per unit volume of the reaction fluid in the reactor.

As the method to increase CHP production per unit volume of the reaction fluid in the reactor, the use of an oxygen-containing gas having higher oxygen content than air as the oxidizing agent is a candidate of the method. However, it seems difficult to realize due to the possibility of explosion or disadvantage of cost performance described above.

SUMMARY OF THE INVENTION

The present invention is aimed at obviating the disadvantages of the prior art. The object of the present invention is to provide a process which is capable of enhancing the CHP production per unit volume of the reaction fluid in the reactor, thus miniaturizing the reactor allowing required CHP production or capable of enhancing the CHP production in an existing reactor.

As a result of the present inventors' earnest studies for solving the above problems, it has been found that (1) by designing a new feed system of oxygen-containing gas, the system can substantially avoid explosion when oxygen-containing gas having higher oxygen content than air is fed, (2) by the feeding of oxygen-containing gas having higher oxygen content than air, the CHP production per unit volume of the reaction fluid in the reactor can significantly increase and (3) the cost increase resulting from oxygen-containing gas having higher oxygen content than air can be compensated with a huge increase of the CHP production per unit volume of the reaction fluid in the reactor and the advantage of the production yield can be rather attained.

In the first aspect of the present invention, there is provided a process for continuous production of cumene hydroperoxide comprising liquid phase oxidation of cumene in a reactor in the presence of an oxygen-containing gas under such conditions that an oxygen content of the total oxygen-containing gas volume fed into the liquid phase in the reactor is adjusted to not less than 22 mol % and not more than 50 mol %, and the cumene hydroperoxide production per unit volume of the reaction fluid in the reactor is not less than 22 kg/m$^3$/hr.

In the second aspect of the present invention, there is provided a process for continuous production of cumene hydroperoxide comprising liquid phase oxidation of cumene in a reactor in the presence of an oxygen-containing gas under such conditions that an oxygen content of the total oxygen-containing gas volume fed into the liquid phase in the reactor is adjusted to not less than 22 mol % and not more than 50 mol %, and an oxygen content of a spent gas of the reactor is not less than 2 mol % and not more than 10 mol %.

In the third aspect of the present invention, there is provided a process for continuous production of cumene hydroperoxide comprising liquid phase oxidation in a reactor in the presence of an oxygen-containing gas under such conditions that an oxygen content of the total oxygen-containing gas volume fed into the liquid phase in the reactor is adjusted to not less than 22 mol % and not more than 50 mol %, and said oxygen-containing gas is fed into the reactor using a sparger whose aperture pitch is at least twice the aperture diameter.

In the fourth aspect of the present invention, there is provided a process for production of phenol comprising decomposition of cumene hydroperoxide obtained any one of the above first to third aspects with acid.

EFFECT OF THE INVENTION

According to the present invention, the process of CHP production by oxidizing cumene in liquid phase enhances the CHP production per unit volume of the reaction fluid in the reactor is capable of miniaturizing the reactor allowing required CHP production or increasing CHP production in an existing reactor.

BEST MODE FOR CARRYING OUT THE INVENTION

The present invention is described in detail below. In the following description, the feature of the present invention will exemplify by preferred embodiments of the present invention and not intended as a definition or the limits of the invention. The CHP production process according to the first to third aspects is the continuous production of cumene hydroperoxide by oxidizing cumene in liquid phase in a reactor in the presence of an oxygen-containing gas. Further, the oxygen content of the total gas fed into the liquid phase in the reactor is adjusted to not less than 22 mol % and not more than 50 mol %. According to the present invention, the oxygen content of the total gas volume fed in a liquid phase is higher than that of air. Common explanations in the first to third aspects are described together as follows.

The oxidation initiator of cumene in the liquid phase is not particularly limited, and usually CHP is used.

The liquid phase oxidation reaction is preferably carried out under multi stage operation using plural reactors connected in series. The number of reactor is not particularly limited, 2 to 5 reactors are preferably used. Cumene is preferably fed to the first reactor continuously and the reactant of the first reactor is fed to the second reactor continuously. Likewise, reactant of (n)th reactor is fed to (n+1)th reactor continuously. The oxygen-containing gas is preferably fed to each reactor continuously. As the reactor, bubbling tower type reactor is generally used but stirring vessel type and bubbling tower with stir type may be also used.

In the above-described liquid phase oxidation, temperature in each reactor is usually adjusted from 50 to 120° C. Each reactor may be set at an optimized temperature. Pressure in each reactor is generally adjusted from 0 to 1 MPaG (gauge pressure). The total residence time in the reactors is usually selected from 3 to 20 hours. By the above-described oxidizing reaction, dimethyl phenyl carbinol (DMPC), acetophenone (AP) etc. except CHP generate as by products. The concentrations of CHP and unreacted cumene in the reactant ejected from the final reactor are usually 20 to 50% by weight and 50 to 80% by weight respectively.

The above-described liquid phase oxidation may be carried out in the presence of catalyst or no catalyst. In the oxidation reaction using catalyst, the kinds of catalyst is not particularly limited and usually basic materials are used. Examples of basic materials may include carbonate and hydroxide compounds of alkali metal such as lithium, sodium and potassium, and alkaline earth metal such as calcium and magnesium. These compounds may be used alone or a mixture of two or more thereof. The state of basic materials used is not particularly limited, usually aqueous solution is used. The amount of catalyst (metal basis) is usually not more than 10 g equivalent, preferably 0.1 to 6 g equivalent per 1 ton of cumene.

In the present invention, the oxygen-containing gas is fed with cumene as a raw material to the reactor (for example, the first one) so as to control the oxygen content of the total gas volume within the range of not less than 22 mole % and not more than 50 mol %. The oxygen-containing gas is preferably fed using a sparger. Sparger is a tube type device having plural apertures to feed and uniformly disperse bubbles of oxygen-containing gas into a reactor. The shape of sparger is not particularly limited, usually a sparger having tubes set in ring type, grid type, radial type or their combination type is used.

In the present invention, the feeding method of oxygen-containing gas is not particularly limited, as long as the oxygen content of the total gas volume is controlled to not less than 22 mol % and not more than 50 mol %. Two or more types of sparger may be used in combination. Namely, there may be adopted other feeding method, in which oxygen-containing gases having different oxygen content or nonoxygen-containing gas are fed using not less than 2 types of spargers so as to control the oxygen content of the fed total gas volume within a range not less than 22 mol % not more than 50 mol % except that the feeding method of oxygen-containing gas having oxygen content not less than 22 mol % not more than 50 mol % using a single sparger. Further, when a single sparger is used, premixed gas, which is prepared by mixing gases through plural pipes connected to the sparger, may be injected from the apertures of the sparger so as to control the oxygen content in the reactor within a range not less than 22 mol % and not more than 50 mol %.

When the oxygen content of the total gas volume fed into a reactor is less than 22 mol %, the technical advantages of enhancement of CHP production according to the present invention cannot be attained. While, the oxygen content of the total gas volume fed into a reactor exceeds 50 mol %, the flow rate of spent gas tends to decrease drastically. This is not preferable that the handling risk due to the occurrence of detonating gas is increased by the fluctuation of reaction condition such as slight drift of reaction temperature. From the standpoint of safety and CHP production, the lower limit of oxygen content of the total gas volume fed into a reactor is preferably 24 mol %, more preferably 26 mol % and the upper limit thereof this is preferably 45 mol %, more preferably 40 mol %.

When hydrocarbon is oxidized at high oxygen content atmosphere, there arise the risk of explosion because the gas composition of the reactor is within the range of explosion. Especially, the gas having this composition is easy to be formed when large size oxygen bubbles are presented in the reaction system. Accordingly, in order to prevent the formation of large size of oxygen babbles, small aperture diameter and long aperture pitch (that means the distance between center of aperture to aperture of the sparger) are preferred. Incidentally, the gas stayed in a certain period of time in the reaction field is safer than new fed due to the lower oxygen content, because oxygen fed into the reactor is consumed just after entering the reaction field.

As the sparger described above, the sparger whose aperture pitch is at least twice, preferably at least four times the aperture diameter is preferred. Use of such sparger may ensure safer operation because it prevent the reaction system from entering into explosion range when the high oxygen content gas is fed into the reactor as oxygen-containing gas. The upper limit of aperture pitch is not particularly limited, and 15 or more times of aperture diameter is preferred. The aperture diameter is usually not less than 1.0 mm, preferably not less than 2.0 mm, usually not more than 8.0 mm, preferably not more than 6.0 mm.

The total gas flow rate per unit volume of the reaction fluid fed into the reactor is usually within a range of 8 to 30 Nl/hr/l.

In the present invention, the preparing method of oxygen-containing gas (oxygen enriched gas) fed into a reactor is not particularly limited. Examples may include a method of mixing two or more sorts of gases to prepare oxygen enriched gas, a method in which two or more kinds of gases fed into the reactor by different methods are mixed at the inside of the reactor, a method chemically or physically enriched oxygen content of oxygen-containing gas such as Pressure Swing Adsorption (PSA) method and oxygen enrich membrane method. According to the above description, the mixing methods of two or more species of gases are disclosed. One is the premixing method outside of the reactor and the other is premixing method inside of the reactor before injecting from sparger. The former method is preferred.

As for the oxygen-containing gas fed into the reactor, preferred is a mixture of gas prepared by mixing with two or more species of gases. Examples of gas components of the mixture may include inactive gases for the reaction such as nitrogen, neon, argon, krypton, xenon, water vapor, active gases for the reaction such as air or oxygen and the mixture of these gases. Preferable combination of gases is mixture of air and oxygen-containing gas having oxygen content exceeded 22 mol %. More preferable one is oxygen enriched air which means mixture of air and oxygen.

When oxygen enriched air prepared by mixing compressed air with oxygen is used as the oxygen-containing gas fed into the reactor, the stable production operation is liable to be disturbed and the amount of the resultant CHP production fluctuates because the absolute value of the oxygen content of the oxygen enriched gas fed into the reactor is fluctuated under long continuous operation due to the fluctuation of the outside conditions such as gas density by the fluctuation of outside temperature or humidity. From this point of view, it is preferable to control the amount of air or oxygen to prepare oxygen enriched gas by analyzing the oxygen content in the oxygen enriched gas so as to minimize the fluctuation of an analytical value of oxygen content in oxygen enriched gas. By controlling the feeding amount of oxygen and/or air, the oxygen content in the oxygen enriched gas can be stabilized and the fluctuation of CHP production due to outside conditions such as temperature or humidity can be minimized.

Controlling method of fed volume of air and/or oxygen is not particularly limited, and a general type of gas flow control systems may be used. Examples of the controlling methods may include a method by controlling the electric power supply to control feed gas volume when using an air compressor, a method by manually or automatically controlling the valve opening-closing of which is set on the way of the gas feed line.

The automatic control system of the valve opening-closing is not particularly limited. For example, there is mentioned a method comprising measuring the oxygen content of oxygen enriched gas before feeding to the reactor by the devices such as gas chromatography or oxygen sensor, analyzing and controlling the obtained concentration value by a computer, and opening-closing the valve equipped on the feed line of air and oxygen before mixing by a remote-control promptly and automatically.

Next, the feature of the first aspect of the present invention is described as follows. The feature of the first aspect is to control the oxygen content of the total gas volume fed into the liquid phase in the reactor to not less than 22 mol % and not more than 50 mol % and to control the CHP production per unit volume of the reaction fluid in the reactor to not less than 22 kg/m$^3$/hr.

The liquid phase oxidation reaction and the method of controlling the oxygen content of the total gas volume fed into the liquid phase in the reactor to not less than 22 mol % and not more than 50 mol % is described in the common explanation of the first to third aspects of the present invention. It is preferable to feed the gas into the liquid phase by the use of single or plural spargers whose aperture pitch is at least twice, preferably at least four times the aperture diameter.

In the first aspect of the present invention, the fed volume of an oxygen-containing gas is preferably controlled based on the oxygen content of spent gas of the reactor, although depending on the oxygen content of the oxygen-containing gas used. Incidentally, spent gas of the reactor means a part of the gas fed into the reactor and spent from the reaction field without consuming oxygen during the reaction field. For example, it directs to the gas held in the gas phase of the reactor or the gas spent from the reactor.

The lower limit of oxygen content of the spent gas of the reactor is usually 2 mol %, preferably 3 mol %. The upper limit thereof is usually 10 mol %, preferably 8 mol %. By keeping the oxygen content within this range the operation can be effectively conducted in safe and economy. When the oxygen content of spent gas of the reactor is less than 2 mol %, the reaction rate tends to decrease drastically. When it exceeds 10 mol %, there arises a higher risk to generate detonating gas.

The controlling method for the oxygen content of spent gas of the reactor is not particularly limited, and there are exemplified a method of adjusting the volume of fed oxygen-containing gas to the reactor and a method of adjusting the reactor temperature so as to control the oxygen consumption. Especially, the temperature adjusting method is preferred because it may control promptly the oxygen content of spent gas of reactor so that the safer production method may be established.

Additionally, the applicant (inventors) of present invention has already disclosed methods of controlling the operation conditions using the composition analysis of the reactant in the reactor or outlet of the reactor by middle wave infrared spectroscopy (for example, refer to Japanese Patent Application Laid-open No. 2003-340270), and a method of analyzing the reactant of the oxidation process of cumene by continuous measurement of near infrared spectroscopy and controlling the reaction condition of the oxidation process of cumene by the analytical results of the measurements (for example, refer to Japanese Patent Application Laid-Open No. 2000-53641). In the present invention, it is preferable in higher yield of the product and safer operation to control the reaction and operation condition using these methods. In this case, especially, it is preferable to adjust the reaction temperature or residence time by monitoring the concentration of CHP as reactant so as to keep CHP concentration constant.

In the first aspect of the present invention, the CHP production per unit volume of the reaction fluid in the reactor is not less than 22 kg/m$^3$/hr, preferably not less than 23 kg/m$^3$/hr. Generally, the reactor for liquid phase reaction has gas phase portion and liquid phase portion. The CHP production per unit volume of the reaction fluid in the reactor means the CHP production per unit volume of the liquid phase portion, per unit time.

The second aspect of the present invention is described as follows. The feature of the second aspect is to control the oxygen content of the total gas volume fed into the liquid phase in the reactor to not less than 22 mol % and not more than 50 mol %, and to control the oxygen content of the spent gas from the reactor to not less than 2 mol % and not more than 10 mol %.

The liquid phase oxidation reaction and the method to control the oxygen content of the total gas volume fed into the liquid phase in the reactor to not less than 22 mol % and not more than 50 mol % is described in the common explanation of the first to third aspects of the present invention. It is preferable to feed the gas into the liquid phase by the use of single or plural spargers whose aperture pitch is at least twice, preferably at least four times the aperture diameter.

In the second aspect of the present invention, the lower limit of oxygen content of the spent gas in the reactor is 2 mol %, preferably 3 mol % and the upper limit thereof is 10 mol %, preferably 8 mol %. By keeping the oxygen content within this range the operation can be effectively conducted in safe and economy. When the oxygen content of spent gas of the reactor is less than 2 mol %, the reaction rate tends to decrease drastically. When it exceeds 10 mol %, there arises a higher risk to generate detonating gas.

In the second aspect of present invention, as is explained in the first aspect, it is preferable in higher yield of the product and safer operation to control the operation condition and reaction condition of the oxidation process using these methods. In this case, especially, it is preferable to adjust the reaction temperature or residence time by monitoring the concentration of CHP as reactant so as to keep CHP concentration constant.

The third aspect of the present invention is described as follows. The feature of the third aspect is to control the oxygen content of the total gas volume fed into the liquid phase in the reactor to not less than 22 mol % and not more than 50 mol %, and to feed the oxygen-containing gas into the reactor by the use of a sparger whose aperture pitch is at least twice the aperture diameter.

The liquid phase oxidation method is described in the common explanation of the first to third aspects of the present invention. In the third aspect of the present invention, it is preferable to feed the gas into the liquid phase of the reactor by the use of single or plural spargers whose aperture pitch is at least twice, preferably at least four times the aperture diameter so as to control the oxygen content of the total gas volume fed into the liquid phase in the reactor to not less than 22 mol % and not more than 50 mol %.

In the third aspect of present invention, as is explained in the first aspect, it is preferable in higher yield of the product and safer operation to control the operation condition and reaction condition of the oxidation process using these methods. In this case, especially, it is preferable to adjust the reaction temperature or residence time by monitoring the concentration of CHP as reactant so as to keep CHP concentration constant.

The method for producing phenol, which is the fourth aspect of the present invention, is described as follows. The feature of process for the production of phenol according to the fourth aspect of the present invention is to use the cumene hydroperoxide obtained in the production method in any one of the first to third aspects in the method of the production of phenol with decomposition of cumene hydroperoxide with acid.

The CHP obtained by the process described in any one of the first to third aspects of the present invention is usually decomposed with acid catalyst such as sulfuric acid (that may be referred to hereinafter as acid decomposition), to give acetone and phenol. Acetone and phenol may be raw materials of production of bisphenol-A independently.

The method for acid decomposition of CHP is not particularly limited, and known methods and their combinations may be adopted. There is exemplified a method comprising concentrating CHP in the mixture until from 70 to 90% by mass based on the CHP mixture obtained by the method according to the present invention, adding sulfuric acid in an amount of 100 to 2000 ppm by mass to the mixture of raw materials of acid decomposition, and acid-decomposing CHP. After the treatment of acid decomposition, the resultant is neutralized with basic compound such as sodium hydroxide aqueous solution, oil phase and aqueous phase are separated, and both fractions are purified by distillation to obtain phenol and acetone.

EXAMPLES

The present invention will be described by examples more detail as follows. However, it is to be understood that the following examples should not serve to limit the present invention as long as not departing from the scope of the present invention.

Example 1

The production of CHP was carried out using three 1 L autoclave type reactor having 100 mm in diameter and 200 mm in height connected in series. A ring type sparger having 2 mm in diameter of aperture, 10 mm in aperture pitch, and 25 apertures was equipped in each reactor.

Raw material comprising 99.0% by weight of cumene and 1.0% by weight of CHP was continuously fed to the first reactor at the feed rate of 100 ml/hr. Then oxygen-containing gas having 30 mol % of oxygen content prepared by mixing 4.96 Nl/hr of air with 0.64 Nl/hr of oxygen in a mixer was fed to each reactor through spargers.

Reaction pressure and residence time of each reactor were controlled at 0.4 MPa (gauge pressure) and for 4 hrs (total residence time was 12 hrs) respectively. Under controlling oxygen content of spent gas of each reactor of 5 mol %, reaction temperature of the first, the second and the third reactor were 105.5° C., 103.0° C. and 102.0° C. respectively.

While monitoring the composition of the reactant at the outlet of reactor using middle wave infrared spectroscopy, reactant was taken out continuously at a rate of 90 g/hr to keep the volume of reaction fluid 400 ml (total volume of reaction fluid was kept 1200 ml).

The composition of reactant at the outlet of reactor was shown in Table 1. CHP production was carried out under the condition of oxidizing efficiency and the CHP production per unit volume of the reaction fluid shown in Table 1. Additionally, oxidizing efficiency is calculated using the following equation. Moreover, flow rate of spent gas, leaking rate of cumene to spent gas and leaking rate of oxygen to spent gas are also shown in Table 1. The operation was able to continue stably for two weeks under the above-described conditions.

Oxidizing Efficiency (%)=CHP production (mol)×
100/(CHP production (mol)+DMPC production
(mol)+AP production (mol))

Comparative Example 1

The same manner as defined in Example 1 was conducted except that air (21 mol % of oxygen content) was used as oxygen-containing gas; air was fed at the rate of 8.0 Nl/hr to be the same total volume of oxygen as in Example 1; reaction temperatures of the first, the second and the third vessel were adjusted to 104.5° C., 102.0° C. and 101.5° C. respectively so that the oxygen content of exhaust gas of each reactor is 5 mol % and reactant was taken out at 88 g/hr, to obtain CHP.

Table 1 shows the composition of reactant, oxidizing efficiency, CHP production per unit volume of the reaction fluid in the reactor flow rate of spent gas, spent gas flow rate, leaking rate of cumene to spent gas and leaking rate of oxygen to spent gas of this case. Although the stable operation was able to carry out for two weeks under the above-described conditions, CHP production efficiency was inferior to Example 1 due to the decrease of residence time and increase of leaking rate of oxygen to spent gas.

Comparative Example 2

The same manner as defined in Example 1 was conducted except that oxygen-containing gas of 60 mol % of oxygen content which was prepared by mixing air of 1.42 Nl/hr with oxygen of 1.38 Nl/hr by mixer was fed so that the total volume of oxygen was same as that of Example 1; reaction temperatures of the first, the second and the third reactor were adjusted to 106.0° C., 103.5° C. and 103.0° C. respectively so that the oxygen content of spent gas of each reactor is 5 mol % and reactant was taken out at 92 g/hr, to obtain CHP.

Table 1 shows the composition of reactant, oxidizing efficiency, the CHP production per unit volume of the reaction fluid in the reactor, the flow rate of spent gas, leaking rate of cumene to spent gas and leaking rate of oxygen to spent gas. The CHP production efficiency was improved comparing to Example 1 due to the increase of resident time and decrease of leaking rate of oxygen to spent gas. However, the operation had to be stopped after two days, because oxygen content of spent gas exceeded 10 mol % due to 1° C. drop of the first vessel temperature.

TABLE 1

|  | Example 1 | Comp. Example 1 | Comp. Example 2 |
|---|---|---|---|
| Composition of reactants (% by weight) | | | |
| CHP | 32.6 | 30.4 | 34.8 |
| DMPC | 1.86 | 1.63 | 2.14 |
| AP | 0.19 | 0.16 | 0.22 |
| Cumene | 65.35 | 67.81 | 62.84 |
| Oxidizing efficiency (%) | 93.2 | 93.6 | 92.7 |
| CHP Production per unit volume of the total reaction fluid (kg/m³/hr) | 23.6 | 21.6 | 26.0 |
| Spent gas flow rate (Nl/hr) | 12.9 | 20.8 | 3.68 |
| Leaking rate of cumene to spent gas (Nl/hr) | 0.52 | 0.82 | 0.15 |
| Leaking rate of oxygen to spent gas (Nl/hr) | 0.65 | 1.04 | 0.18 |

Consequently, the CHP production may be carried out stably with increasing the CHP production per unit volume of the reaction fluid in the reactor by means of the present invention. Especially, setting the oxygen content of the total gas volume fed into the reactor higher than air, ranging from not less than 22 mol % and not more than 50 mol %, results in the increase of residence time and decrease of leaking rate of oxygen to spent gas so that the CHP production may increase by not less than 9% comparing the use of air as oxygen-containing gas.

While the present invention has been described with reference to embodiments which are the most practical now and preferred, it is to be understood that the present invention is not limited to the specific embodiments, various changes and modification may be made properly in the present invention without departing from the spirit or scope which is legible from the claims and the whole specification and all such changes is included in the present invention. Additionally, the present invention is based on Japanese Patent Application (Application No. 2004-60904) filed Mar. 4, 2004 and it is cited as reference.

What is claimed is:

1. A process for continuous production of cumene hydroperoxide comprising liquid phase oxidation of cumene in a reactor in the presence of an oxygen-containing gas under such conditions that an oxygen content of the total oxygen-containing gas volume fed into the liquid phase in the reactor is adjusted to not less than 22 mol % and not more than 50 mol %, and the cumene hydroperoxide production per unit volume of the reaction fluid in the reactor is not less than 22 kg/m³/hr.

2. A process according to claim 1, wherein the gas fed into the liquid phase in the reactor is a mixture of two or more gases.

3. A process according to claim 1, wherein the gas fed into the liquid phase in the reactor is an oxygen enriched air which is a mixture of air with oxygen.

4. A process according to claim 1, wherein an oxygen content of a spent gas of the reactor is not less than 2 mol % and not more than 10 mol %.

5. A process according to claim 1, wherein the oxygen-containing gas is fed into the reactor using a sparger whose aperture pitch is at least twice the aperture diameter.

6. A process for continuous production of cumene hydroperoxide comprising liquid phase oxidation of cumene in a reactor in the presence of an oxygen-containing gas under such conditions that an oxygen content of the total oxygen-containing gas volume fed into the liquid phase in the reactor is adjusted to not less than 22 mol % and not more than 50 mol %, and an oxygen content of a spent gas of the reactor is not less than 2 mol % and not more than 10 mol %.

7. A process according to claim 6, wherein the gas fed into the liquid phase in the reactor is a mixture of two or more gases.

8. A process according to claim 6, wherein the gas fed into the liquid phase in the reactor is an oxygen enriched air which is a mixture of air with oxygen.

9. A process according to claim 6, wherein the oxygen-containing gas is fed into the reactor using a sparger whose aperture pitch is at least twice the aperture diameter.

10. A process for continuous production of cumene hydroperoxide comprising liquid phase oxidation in a reactor in the presence of an oxygen-containing gas under such conditions that an oxygen content of the total oxygen-containing gas volume fed into the liquid phase in the reactor is adjusted to not less than 22 mol % and not more than 50 mol %, and said oxygen-containing gas is fed into the reactor using a sparger whose aperture pitch is at least twice the aperture diameter.

11. A process according to claim 10, wherein the gas fed into the liquid phase in the reactor is a mixture of two or more gases.

12. A process according to claim 10, wherein the gas fed into the liquid phase in the reactor is an oxygen enriched air which is a mixture of air with oxygen.

13. A process for production of phenol comprising acid decomposition of cumene hydroperoxide obtained claim 1.

* * * * *